United States Patent
Jerussi et al.

(10) Patent No.: US 9,072,699 B2
(45) Date of Patent: *Jul. 7, 2015

(54) TREATMENT OF CNS DISORDERS WITH TRANS 4-(3,4-DICHLOROPHENYL)-1,2,3,4-TETRAHYDRO-1-NAPTHALENAMINE

(71) Applicant: Sunovion Pharmaceuticals Inc., Marlborough, MA (US)

(72) Inventors: Thomas Jerussi, Charleston, SC (US); Qun Kevin Fang, Wellesley, MA (US); Mark G. Currie, Sterling, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/152,377

(22) Filed: Jan. 10, 2014

(65) Prior Publication Data

US 2014/0128474 A1    May 8, 2014

Related U.S. Application Data

(63) Continuation of application No. 13/693,489, filed on Dec. 4, 2012, now Pat. No. 8,658,700, which is a continuation of application No. 13/365,565, filed on Feb. 3, 2012, now Pat. No. 8,344,030, which is a continuation of application No. 12/847,270, filed on Jul. 30, 2010, now Pat. No. 8,134,029, which is a continuation of application No. 12/538,583, filed on Aug. 10, 2009, now Pat. No. 7,790,772, which is a continuation of application No. 12/173,626, filed on Jul. 15, 2008, now Pat. No. 7,589,237, which is a continuation of application No. 11/416,586, filed on May 3, 2006, now Pat. No. 7,423,179, which is a continuation of application No. 11/338,191, filed on Jan. 24, 2006, now abandoned, which is a continuation of application No. 11/220,891, filed on Sep. 7, 2005, now Pat. No. 7,105,699, which is a continuation of application No. 10/663,173, filed on Sep. 16, 2003, now Pat. No. 7,087,785.

(60) Provisional application No. 60/411,305, filed on Sep. 16, 2002, provisional application No. 60/411,304, filed on Sep. 16, 2002.

(51) Int. Cl.
*A61K 31/135* (2006.01)
*C07C 211/42* (2006.01)

(52) U.S. Cl.
CPC ........... *A61K 31/135* (2013.01); *C07B 2200/07* (2013.01); *C07C 211/42* (2013.01); *C07C 2102/10* (2013.01)

(58) Field of Classification Search
None
See application file for complete search history.

(56) References Cited

U.S. PATENT DOCUMENTS

| | | |
|---|---|---|
| 4,556,676 A | 12/1985 | Welch, Jr. et al. |
| 4,608,382 A | 8/1986 | Ferrini et al. |
| 4,634,703 A | 1/1987 | Kurtz et al. |
| 4,687,772 A | 8/1987 | Alderdice |
| 4,981,870 A | 1/1991 | Koe |
| 5,061,728 A | 10/1991 | Koe |
| 5,468,749 A | 11/1995 | Gawin et al. |
| 5,858,407 A | 1/1999 | Ayer et al. |
| 6,136,824 A | 10/2000 | MacLeod et al. |
| 6,245,782 B1 | 6/2001 | Serebruany et al. |
| 6,451,788 B1 | 9/2002 | Horrobin et al. |
| 6,506,940 B1 | 1/2003 | Jadav et al. |
| 7,087,785 B2 | 8/2006 | Jerussi et al. |
| 7,105,699 B2 | 9/2006 | Jerussi |
| 7,423,179 B2 | 9/2008 | Jerussi et al. |
| 7,589,237 B2 | 9/2009 | Jerussi et al. |
| 7,790,772 B2 | 9/2010 | Jerussi et al. |
| 8,134,029 B2 * | 3/2012 | Jerussi et al. .............. 564/308 |
| 2003/0078262 A1 | 4/2003 | Taylor |
| 2004/0077864 A1 | 4/2004 | Kim et al. |
| 2004/0087661 A1 | 5/2004 | Jerussi et al. |
| 2006/0128993 A1 | 6/2006 | Jerussi et al. |
| 2006/0216799 A1 | 9/2006 | Jerussi et al. |
| 2007/0282007 A1 | 12/2007 | Tarantino et al. |
| 2008/0262071 A1 | 10/2008 | Dinan et al. |
| 2008/0293726 A1 | 11/2008 | Caron et al. |

FOREIGN PATENT DOCUMENTS

| | | |
|---|---|---|
| EP | 0028901 A1 | 5/1981 |
| EP | 0285008 | 10/1988 |
| EP | 0442423 | 8/1991 |
| EP | 0497314 | 8/1992 |
| EP | 1262197 | 12/2002 |
| JP | 58010518 | 1/1983 |
| JP | 03246225 | 11/1991 |

(Continued)

OTHER PUBLICATIONS

W.M. Welch et al., "Nontricyclic Antidepressant Agents Derived from cis-and trans-1-Amino-4-aryltetralins", J. Med. Chem., 27, 1508-1515 (1984).

(Continued)

*Primary Examiner* — Brian J Davis

(74) *Attorney, Agent, or Firm* — Heslin, Rothenberg, Farley & Mesiti, P.C.

(57) ABSTRACT

Treatment of CNS disorders with (1R,4S)-trans 4-(3,4-dichlorophenyl)-1,2,3,4-tetrahydro-1-napthalenamine; and (1S,4R)-trans 4-(3,4-dichlorophenyl)-1,2,3,4-tetrahydro-1-napthalenamine is disclosed. A process for preparing 4-(3,4-dichlorophenyl)-1,2,3,4-tetrahydro-1-napthalenamine is also disclosed. The process includes the preparation of all four isomers of N-[4-(3,4-dichlorophenyl)-1,2,3,4-tetrahydronaphthalen-1-yl]formamide, which are also useful.

6 Claims, No Drawings

(56) References Cited

FOREIGN PATENT DOCUMENTS

| JP | 2002020291 | 1/2002 |
|---|---|---|
| JP | 2003335678 | 11/2003 |
| WO | 97/31629 | 9/1997 |
| WO | 03/007956 | 1/2003 |
| WO | 03/065970 | 8/2003 |
| WO | 2004/024130 | 3/2004 |
| WO | 2004/024669 A1 | 3/2004 |
| WO | 2007/006003 | 1/2007 |
| WO | 2007/030589 | 3/2007 |
| WO | 2007/143267 A1 | 12/2007 |
| WO | 2010/132521 | 11/2010 |
| WO | 2011/069032 | 6/2011 |

OTHER PUBLICATIONS

V.L. Serebruany et al., "Platelet Inhibition by Sertraline and N-Desmethylsertraline: A Possible Missing Link Between Depression, Coronary Events, and Mortality Benefits of Selective Serotonin Reuptake Inhibitors", Pharmacological Research, 43 (5), 453-461 (2001).
B.A. Hamelin et al., "The dispostion of fluoxetine but not sertraline is altered in poor metabolizers of debrisoquin", Clinical Pharmacology & Therapeutics, 60 (5), 512-521 (1996).
R.A. Ronfeld et al., "Pharmacokinetics of Sertraline and its N-Demethyl Metabolite in Elderly and Young Male and Female Volunteers", Clinical Pharmacokinet, 32, 22-30 (1997).
C. Sanchez and J. Hyttel, "Comparison of the Effects of Antidepressants and Their Metabolites on Reuptake of Biogenic Amines and on Receptor Binding", Cellular and Molecular Neurobiology, 19, (4), 467-489, (1999).
B.K. Koe et al., "Sertraline, 1S,4S-N-Methyl-4-(3,4-Dichlorophenyl)-1,2,3,4-Tetrahydro-1-Naphthylamine, a New Uptake Inhibitor with Selectivity for Serotonin", The Journal of Pharmacology and Experimental Therapeutics 226, (3), 686-700, (1983).
Communication pursuant to Article 96(2) EPC, dated Nov. 30, 2007 from the European Patent Office for European counterpart Application No. 03754641.3-2103, cover page and pp. 1-5.
Andersen, Peter H. "Biochemical and Pharmacological Characterization of [$^3$H]GBR 12935 Binding In Vitro to Rat Striatal Membranes: Labeling of the Dopamine Uptake Complex", J. or Neurochemistry, 48, 1887-1896, (1987).
Clague et al. "Action of Agonists and Antagonists at Muscarinic Receptors Present on Ileum and Atria In Vitro". British J. of Pharmacology, 86, 163-170 (1985).
Deninno et al. "The Preparation and Intra- and Intermolecular Addition Reactions of Acyclic N-Acylimines: Application to the Synthesis of (±)-Sertraline". J. Organic Chemistry, 66, 6988-6993 (2001).
Dews, Peter B. "The Measurement of the Influence of Drugs on Voluntary Activity in Mice". Brit. J. of Pharmacology, 8, 46-48 (1953).
Fuller et al. "Comparison of Desmethylsertraline With Sertraline as a Monoamine Uptake Inhibitor In Vivo". Prog. Neuro-Psychopharmacol. & Biol. Psychiatry, vol. 19, 135-149 (1995).
Galli et al. "Sodium-Dependent Norepinephrine-Induced Currents in Noreprinephrine-Transporter-Transfected HEK-293 Cells Blocked by Cocaine and Antidepressants". J. of Exper. Biology, 198, 2197-2212 (1995).
Giros et al. "Cloning, Pharmacological Characterization, and Chromosome Assignment of the Human Dopamine Transporter". Molecular Pharmacology, 42, 383-390 (1992).
Gonzalez-Viejo et al. "A Comparative Study of Fibromyalgia Treatmeant: Ultrasonography and Physiotherapy Versus Sertraline Treatment". Annales de réadaption et de médecine physique, 48, 610-615 (2005).
Goodnick et al. "Sertraline in Diabetic Neuropathy: Preliminary Results". Annals of Clin. Psychiatry, vol. 9, No. 4, 255-257 (1997).
Gu et al. "Stable Expression of Biogenic Amine Transporters Reveals Differences in Inhibitor Sensitivity, Kinetics, and Ion Dependence". J. of Biol. Chem., vol. 269, No. 10, 7124-7130 (1994).

Harrison et al. "Compendium of Organic Synthetic Methods", 258-259 (1971).
Lifschytz et al. "Sex-dependent Effects of Fluoxetine and Triiodothyronine in the Forced Swim Test in Rats". Euro. Nueropsychopharmacology, 16, 115-121 (2006).
Maehr, Hubert. "A Proposed New Convention for Graphic Presentation of Molecular Geometry and Topography". J. of Chem. Educ., 62, 114-120 (1985).
Janowsky et al. "Characterization of Sodium-Dependent [3H]GBR-12935 Binding in Brain: A Radioligand for Selective Labelling of the Dopamine Transport Complex". J. of Neurochemistry, 46, 1272-1276 (1986).
Kim and Chung. "An Experimental Model for Peripheral Neuropathy Produced by Segmental Spinal Nerve Litigation in the Rat", 50, 355-363 (1992).
Pacholczyk et al. "Expression Cloning of a Cocaine- and Antidepressant-sensitive Human Noradrenaline Transporter". Letters to Nature, vol. 350, 350-354 (1991).
Perovic & Muller. "Pharmacological Profile of Hypericum Extract". Arzneim.-Forsch/Drug Res. 45, Nr. 11, 1145-1148 (1995).
Porsolt et al. "Behavioural Despair in Mice: a Primary Screening Test for Antidepressants". Arch Int. Pharmacdoyn, 229, 327-336 (1977).
Pristupa et al. "Pharmacological Heterogeneity of the Cloned and Native Human Dopamine Transporter: Disassociation of [3H]WIN 35,428 and [3H]GBR 12,935 Binding". ASPET. 45, 125-135 (1994).
Semenchuk et al. "Double-blind, Randomized Trial of Bupropion SR for the Treatment of Neuropathic Pain". Neurology, 57, 1583-1588 (2001).
Tang et al. "An Ortho-substituted BIPHEP ligand and its Applications in Rh-Catalyzed Hydrogenation of Cyclic Enamides". Organic Letters, 4(10), 1695-1698 (2002).
Tatsumi et al. "Pharmacological Profile of Antidepressants and Related Compounds at Human Monoamine Transporters". Euro. J. of Pharma., 340, 249-258 (1997).
Vazquez-Palacios et al. "Antidepressant-like Effects of the Acute and Chronic Administration of Nicotine in the Rat Forced Swimming Test and its Interaction with Flouxetine". Pharmacology, Biochemistry and Behavior, 78, 165-169 (2004).
Wheeler-Aceto et al. "Standardization of the Rat Paw Formalin Test for the Evaluation of Analgesics". Psychopharmacology, 104, 35-44 (1991).
Witchel et al. "Inhibitory Actions of the Selective Serotonin Reuptake Inhibitor Citalopram on HERG and Ventricular L-type Calcium Currents". FEBS Letters 512, 59-66 (2002).
Wong et al. "Norfluoxetine Enantiomers as Inhibitors of Serotonin Uptake in Rat Brain". Neuropsychopharmacology, vol. 8, No. 4, 337-344 (1993).
Yaksh et al. "An Automated Flinch Detecting System for Use in the Formalin Nociceptive Bioassay". J. Appl. Physiol., 90, 2386-2402 (2001).
Notice of Allowance for U.S. Appl. No. 11/416,586 dated Apr. 29, 2008.
ISR & WO for International Patent Application No. PCT/US07/65585 dated Oct. 3, 2008.
ISR & WO for International Patent Application No. PCT/US03/29110 dated Mar. 2, 2004.
Childers et al. "Lecozotan Hydrochloride: Cognition Enhancer, Treatment of Alzheimer's Disease, Competitive 5-HT1A Receptor Antagonist", *Drugs of the Future*, 32(5), 339-407 (2007).
Emsley, Robin, "Drugs in Development for the Treatment of Schizophrenia," Expert Opin, Investig. Drugs, 18(8), 1103-1118 (2009).
McKelvy, J.F., "AV965, A Selective 5-HT1A Silent Antagonist as a Candidate for Adjunctive Treatment of Cognitive Impairment in Schizophrenia," International Congress of Schizophrenia Research, Schizophrenia Bulletin, 31(2), 305 (2005).
Jadev et al., "A Process for Converting Stereoisomers of Sertraline into Sertaline" CAPLUS Chemical Patent Abstract 2001; 507 654, publication date 2001.

* cited by examiner

TREATMENT OF CNS DISORDERS WITH TRANS 4-(3,4-DICHLOROPHENYL)-1,2,3,4-TETRAHYDRO-1-NAPTHALENAMINE

CROSS REFERENCE TO RELATED APPLICATIONS

This application is a continuation application of co-pending U.S. application Ser. No. 13/693,489, filed on Dec. 4, 2012, now U.S. Pat. No. 8,658,700. U.S. application Ser. No. 13/693,489 was a continuation application of U.S. application Ser. No. 13/365,565, filed on Feb. 3, 2012, now U.S. Pat. No. 8,344,030. U.S. application Ser. No. 13/365,565 was a continuation of U.S. application Ser. No. 12/847,270, filed Jul. 30, 2010, now U.S. Pat. No. 8,134,029. U.S. application Ser. No. 12/847,270 was a continuation of U.S. application Ser. No. 12/538,583 filed on Aug. 10, 2009, now U.S. Pat. No. 7,790,772, which was a continuation of U.S. application Ser. No. 12/173,626, filed on Jul. 15, 2008, now U.S. Pat. No. 7,589,237 which was a continuation of U.S. application Ser. No. 11/416,586, filed on May 3, 2006, now U.S. Pat. No. 7,423,179. U.S. application Ser. No. 11/416,586 was a continuation of U.S. application Ser. No. 11/338,191, filed on Jan. 24, 2006, which was a continuation of U.S. application Ser. No. 11/220,891, filed on Sep. 7, 2005, now U.S. Pat. No. 7,105,699, which was a continuation of U.S. application Ser. No. 10/663,173, filed on Sep. 6, 2003, now U.S. Pat. No. 7,087,785, and claimed the priority of provisional applications 60/411,304 and 60/411,305, both filed Sep. 16, 2002. The entire disclosures of all of the prior applications and patents are incorporated herein by reference.

FIELD OF THE INVENTION

The present invention relates to methods of treating central nervous system (CNS) disorders using (1R,4S)-trans 4-(3,4-dichlorophenyl)-1,2,3,4-tetrahydro-1-napthalenamine; (1S,4R)-trans 4-(3,4-dichlorophenyl)-1,2,3,4-tetrahydro-1-napthalenamine and the four isomers of N-[4-(3,4-dichlorophenyl)-1,2,3,4-tetrahydronaphthalen-1-yl] formamide.

BACKGROUND OF THE INVENTION

Clinicians recognize a distinction among central nervous system illnesses, and there have been many schemes for categorizing mental disorders. The *Diagnostic and Statistical Manual of Mental Disorders, Fourth Ed., Text Revision*, (hereinafter, the "DSM-IV-TR™"), published by the American Psychiatric Association, and incorporated herein by reference, provides a standard diagnostic system upon which persons of skill rely. According to the framework of the DSM-IV-TR™, the CNS disorders of Axis I include: disorders diagnosed in childhood (such as, for example, attention deficit disorder or "ADD" and attention deficit/hyperactivity disorder or "ADHD") and disorders diagnosed in adulthood. CNS disorders diagnosed in adulthood include (1) schizophrenia and psychotic disorders; (2) cognitive disorders; (3) mood disorders; (4) anxiety related disorders; (5) eating disorders; (6) substance related disorders; (7) personality disorders; and (8) "disorders not yet included" in the scheme.

Of particular interest to the present invention are adulthood disorders of DSM-IV-TR™ categories (1) through (7) and sexual disorders, currently classified in category (8). Mood disorders of particular interest include depression, seasonal affective disorder and bipolar disorder. Anxiety related disorders of particular interest are agoraphobia, generalized anxiety disorder, phobic anxiety, obsessive compulsive disorder (OCD), panic disorder, acute stress disorder, posttraumatic stress disorder, premenstrual syndrome, social phobia, chronic fatigue disorder, perimenopause, menopause and male menopause.

In general, treatment for psychoses, such as schizophrenia, for example, is quite different than treatment for mood disorders. While psychoses are treated with $D_2$ antagonists such as olanzapine (the "typical" and "atypical" antipsychotics), mood disorders are treated with drugs that inhibit the neuronal reuptake of monoamines, in particular, serotonin (5-HT), norepinephrine (NE) and dopamine (DA).

Common therapeutic agents for mood disorders include, but are not limited to, selective serotonin reuptake inhibitors (SSRI's), including fluoxetine, citalopram, nefazodone, fluvoxamine, paroxetine, and sertraline.

Sertraline, whose chemical name (1S,4S)-cis 4-(3,4-dichlorophenyl)-1,2,3,4-tetrahydro-N-methyl-1-napthalenamine, is approved for the treatment of depression by the United States Food and Drug Administration, and is available under the trade name ZOLOFT® (Pfizer Inc., NY, N.Y., USA). In the human subject, sertraline has been shown to be metabolized to (1S,4S)-cis 4-(3,4-dichlorophenyl)-1,2,3,4-tetrahydro-1-napthalenamine, also known as desmethylsertraline or norsertraline. Desmethylsertraline has been described as "not contributing significantly to the serotonergic action of sertraline" Ronfield et al., *Clinical Pharmacokinetcs*, 32:22-30 (1997). Reports from Hamelin et al., *Clinical Pharmacology & Therapeutics*, 60:512 (1996) and Serebruany et al., *Pharmacological Research*, 43:453-461 (2001), have stated that norsertraline is "neurologically inactive". These statements appear to be based on results observed in serotonin-induced syndrome and ptosis in mouse models in vivo, whereas the original Pfizer research papers suggested on the basis of data in vitro that desmethylsertraline was a selective serotonin uptake inhibitor. Koe et al., *JPET*, 226: 686-700 (1983). Sanchez et al., *Cellular and Molecular Neurobiology*, 19: 467 (1999), speculated that despite its lower potency, desmethylsertraline might play a role in the therapeutic effects of sertraline but, there is presently no evidence in the literature to support this theory.

The primary clinical use of sertraline is in the treatment of depression. In addition, U.S. Pat. No. 4,981,870 discloses and claims the use of sertraline and norsertraline, as well as (1R, 4S)-trans 4-(3,4-dichlorophenyl)-1,2,3,4-tetrahydro-N-methyl-1-napthalenamine and (1S,4R)-trans 4-(3,4-dichlorophenyl)-1,2,3,4-tetrahydro-N-methyl-1-napthalenamine for the treatment of psychoses, psoriasis, rheumatoid arthritis and inflammation. The receptor pharmacology of the individual (1S,4R) and (1R,4S) enantiomers of trans 4-(3,4-dichlorophenyl)-1,2,3,4-tetrahydro-N-methyl-1-napthalenamine is described by Welch et al., *J. Med. Chem.*, 27:1508-1515 (1984).

SUMMARY OF THE INVENTION

It has now been discovered that (1R,4S)-trans 4-(3,4-dichlorophenyl)-1,2,3,4-tetrahydro-1-napthalenamine (P) and (1S,4R)-trans 4-(3,4-dichlorophenyl)-1,2,3,4-tetrahydro-1-napthalenamine (Q) are useful in the treatment of CNS-related disorders that are modulated by monoamine activity, and produce diminished side effects as compared to the current standards of treatment. Treatable CNS disorders include, but are not limited to, mood disorders (e.g., depression), anxiety disorders (e.g., OCD), behavioral disorders (e.g., ADD and ADHD), eating disorders, substance abuse disorders and sexual function disorders. The compounds are also useful for the prophylaxis of migraine.

Compounds P and Q are represented by the formulae:

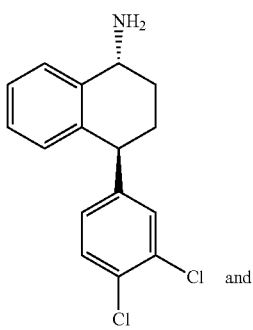

P

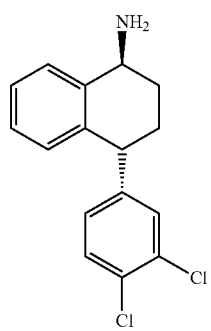

Q

In one aspect, the present invention relates to a method for treating CNS disorders, which involves the administration of a therapeutically effective amount of P or Q, or a pharmaceutically acceptable salt of either.

In another aspect, the invention relates to trans-4-(3,4-dichlorophenyl)-1,2,3,4-tetrahydro-1-napthalenamine of the formula (PQ):

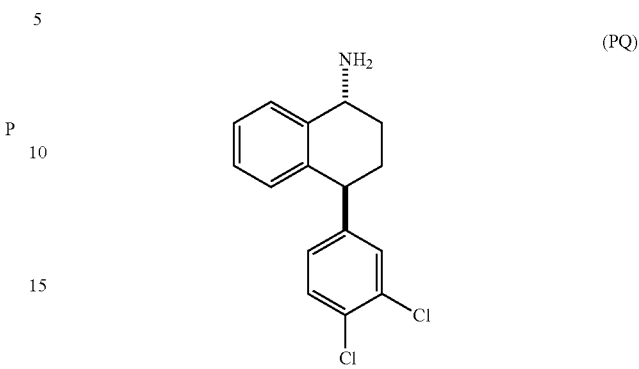

(PQ)

In another aspect, the invention relates to a process for preparing 4-(3,4-dichlorophenyl)-1,2,3,4-tetrahydro-1-napthalenamine, which involves:
(a) reacting 4-(3,4-dichlorophenyl)-3,4-dihydro-1-naphthalenone with an excess of formic acid and formamide to provide N-[4-(3,4-dichloro phenyl)-1,2,3,4-tetrahydronaphthalen-1-yl]formamide; and
(b) hydrolyzing the N-[4-(3,4-dichlorophenyl)-1,2,3,4-tetrahydro naphthalen-1-yl]formamide with aqueous acid, and thereby yielding 4-(3,4-dichlorophenyl)-1,2,3,4-tetrahydro-1-napthalenamine.

DETAILED DESCRIPTION OF THE INVENTION

The present invention provides several embodiments of a method for treating one or more CNS disorders. The method encompasses administering pure P or pure Q, or any mixture thereof. Administration of either compound or any combination thereof, including the racemic mixture of trans isomers, results in a broad therapeutic profile and avoidance of side effects that are associated with an imbalance among the distribution of activity between norepinephrine, serotonin and dopamine receptors.

Preparation of compounds of the present invention is illustrated below in Scheme 1 and its accompanying narrative.

Scheme 1

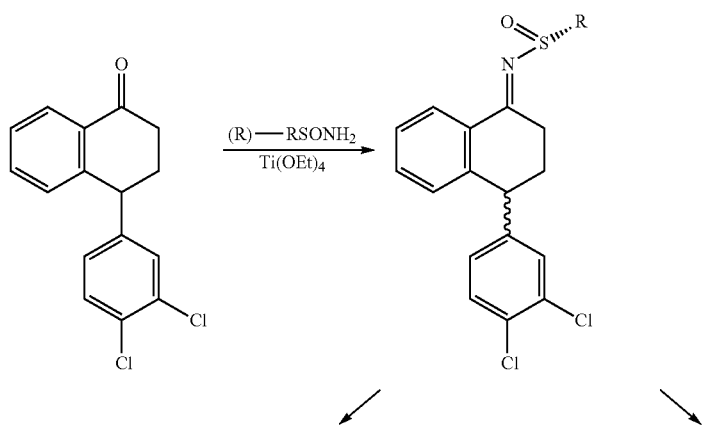

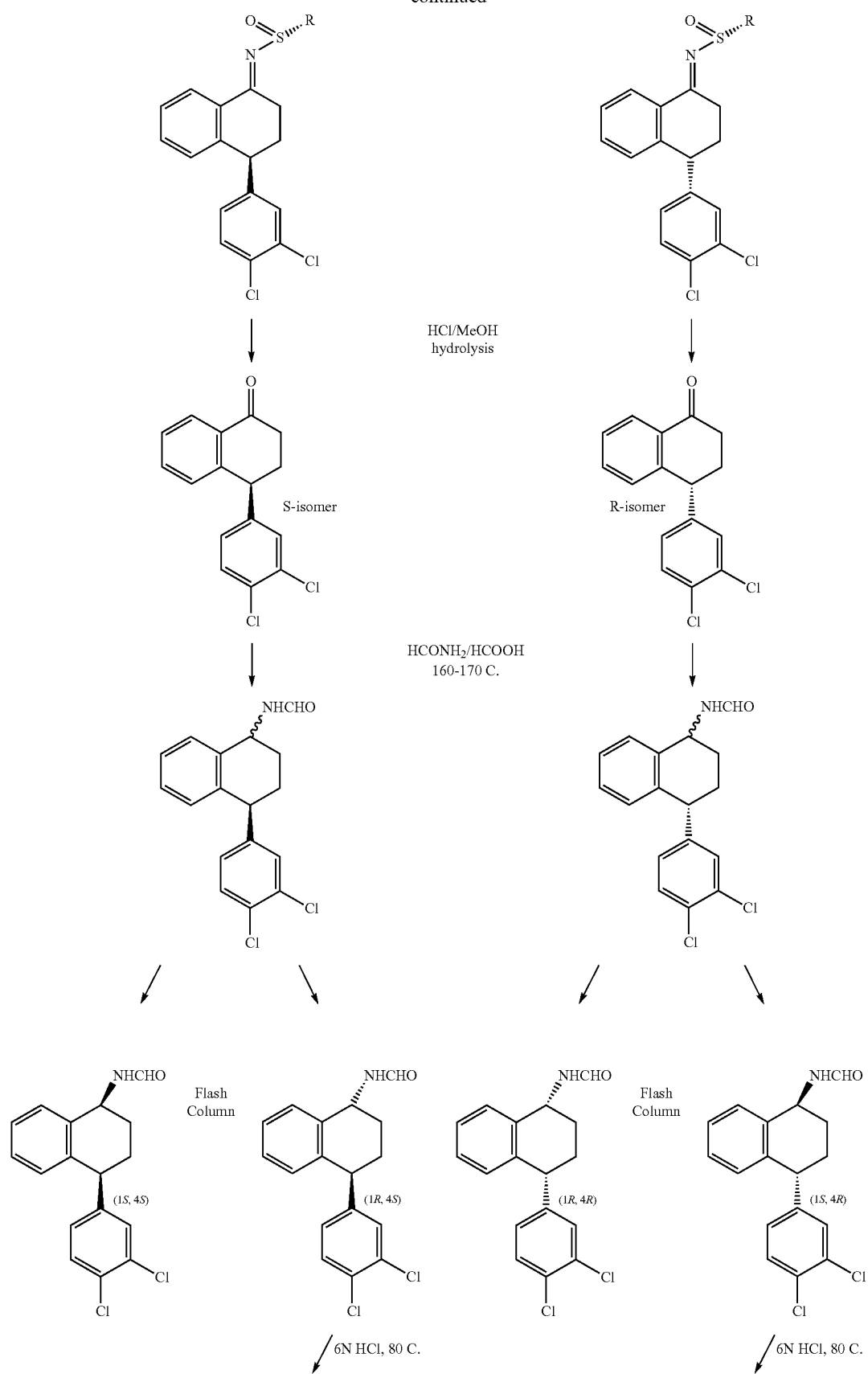

-continued

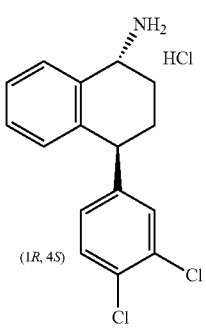
(1R, 4S)

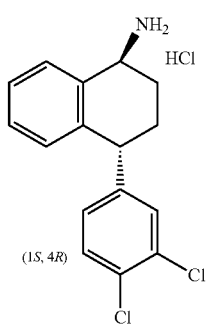
(1S, 4R)

In the compound

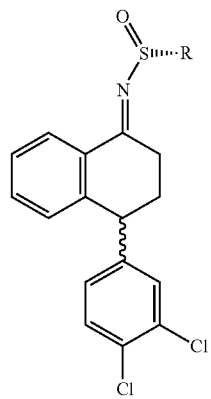

of Scheme 1, R is

wherein $R^1$, $R^2$ and $R^3$ are each independently alkyl. In a preferred embodiment of the compounds, R is tert-butyl.

N-[4-(3,4-dichlorophenyl)-1,2,3,4-tetrahydronaphthalen-1-yl]formamide, the intermediate in the synthesis shown in Scheme 1, exists in four stereoisomeric forms:

A

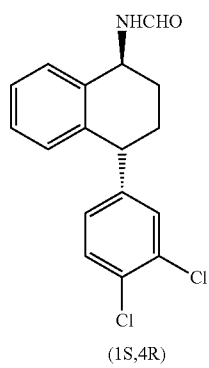
(1S,4R)

-continued

B

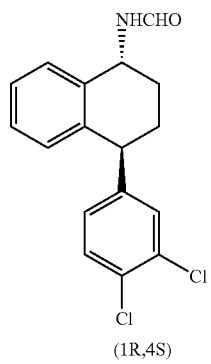
(1R,4S)

C

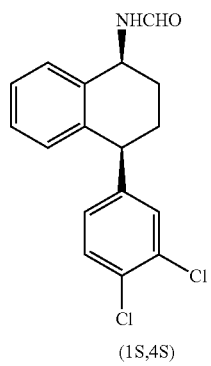
(1S,4S)

D

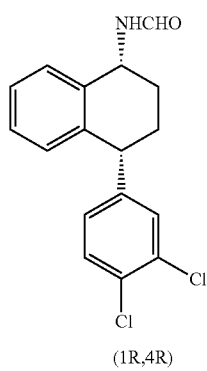
(1R,4R)

When N-[4-(3,4-dichlorophenyl)-1,2,3,4-tetrahydronaphthalen-1-yl]formamide is synthesized from achiral starting materials via non-stereoselective syntheses, all four isomers will be produced. The mixture can be readily separated into a racemic cis diastereomer and a racemic trans diastereomer by means, such as recrystallization or chromatography on achiral media, that rely on chemical and physical differences.

The trans diastereomer, represented as E below, is a 1:1 mixture of A and B. When E is hydrolyzed, PQ is produced; when A is hydrolyzed, P is produced; when B is hydrolyzed, Q is produced. The cis diastereomer, represented as F below, is a 1:1 mix of C and D.

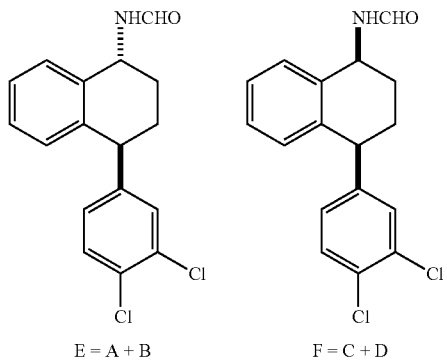

E = A + B     F = C + D

The graphic representations of racemic, ambiscalemic and scalemic or enantiomerically pure compounds used herein are taken from Maehr, *J. Chem. Ed.*, 62:114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

Thus, formula PQ above indicates any mixture of the individual isomers P and Q, which share the trans relative configuration. Clearly, the most convenient mixture is the 1:1 racemate. When a single enantiomer is to be employed, it is preferred that the mixture include greater than 90% of the desired enantiomer, more preferably greater than 95%, and most preferably, greater than 98%. The percentages refer to the optical purity of the single enantiomer.

According to the present invention a therapeutically effective amount of N-[4-(3,4-dichlorophenyl)-1,2,3,4-tetrahydronaphthalen-1-yl]formamide, which may be a pure isomer or a mixture of any or all of A, B, C and D, may also be administered to a person in need of therapy.

Disorders treatable with the compounds of the present invention include, but are not limited to: depression, bipolar disorder, chronic fatigue disorder, seasonal affective disorder, agoraphobia, generalized anxiety disorder, phobic anxiety, obsessive compulsive disorder (OCD), panic disorder, acute stress disorder, social phobia, posttraumatic stress disorder, premenstrual syndrome, menopause, perimenopause and male menopause.

Depression, for example, is characterized by changes in mood, and by feelings of intense sadness or pessimistic worry. Symptoms include insomnia, anorexia, CNS slowing, as well as a loss of drive, enthusiasm, and libido.

Studies have shown that an increase in body monoamine levels, especially an increase in the level of norepinephrine, appears to reduce the symptoms associated with the aforementioned disorders. Thus, the compounds of the present invention are believed to provide their therapeutic activity by simultaneously blocking the reuptake of norepinephrine, serotonin and dopamine.

In addition to their beneficial therapeutic effects, compounds of the present invention provide the additional benefit of avoiding one or more of the adverse effects associated with conventional mood disorder treatments. Such side effects include, for example, insomnia, breast pain, weight gain, extrapyramidal symptoms, elevated serum prolactin levels and sexual dysfunction (including decreased libido, ejaculatory dysfunction and anorgasmia).

The compounds of the present invention are also effective for treating disruptive behavior disorders, such as attention deficit disorder (ADD) and attention deficit disorder/hyperactivity (ADHD), which is in accordance with its accepted meaning in the art, as provided in the DSM-IV-TR™. These disorders are defined as affecting one's behavior resulting in inappropriate actions in learning and social situations. Although most commonly occurring during childhood, disruptive behavior disorders may also occur in adulthood.

The term ADD, as used herein, includes both attention deficit disorder and attention deficit/hyperactivity disorder (ADHD), and is used in accordance with its accepted meaning in the art, which is defined in the DSM-IV-TR™. Accordingly, as used herein, the term attention deficit disorder includes ADHD:DSM-IV-TR™ categories 314.xx (which includes 314.01, 314.00 and 314.9); conduct disorder: DSM-IV-TR™ categories 312.xx (which includes 312.81, 312.82 and 312.89, as well as 312.9-disruptive behavior disorder); and oppositional defiant disorder: DSM-IV-TR™ category 313.81. The skilled artisan will recognize that there are alternate nomenclatures, nosologies, and classification systems for pathological conditions and that these systems evolve with medical scientific progress.

Methylphenidate (RITALIN®; Novartis Pharmaceuticals Corporation, East Hanover, N.J., USA) is typically the drug of choice for the treatment and/or prevention of ADD. Tricyclic antidepressants (such as, for example, imipramine), caffeine, dextroamphetamine, and other psychostimulants (such as, for example, pemoline) are less preferred alternatives to methylphenidate. Common side effects of methylphenidate include sleep disturbances, depression or sadness, headache, stomachache, suppression of appetite, elevated blood pressure, and, with large continuous doses, a reduction of growth. Accordingly, alternate means of treating or preventing attention deficit disorders would be of great benefit. Due to their strong dopaminergic component, compounds of the present invention not only provide effective treatment of disruptive behavior disorders, but also, avoid many of the adverse effects associated with conventional treatments.

The term "treating" when used in connection with the foregoing disorders means amelioration, prevention or relief from the symptoms and/or effects associated with these disorders and includes the prophylactic administration of a compound of formula P or Q, a mixture thereof, or a pharmaceutically acceptable salt of either, to substantially diminish the likelihood or seriousness of the condition.

Compounds of the present invention are also effective for treating eating disorders. Eating disorders are defined as a disorder of one's appetite or eating habits or of inappropriate somatotype visualization. Eating disorders include, but are not limited to, anorexia nervosa; bulimia nervosa, obesity and cachexia.

Compounds of the invention are also effective for treating cerebral function disorders. The term cerebral function disorder, as used herein, includes cerebral function disorders involving intellectual deficits, and may be exemplified by senile dementia, Alzheimer's type dementia, memory loss, amnesia/amnestic syndrome, epilepsy, disturbances of consciousness, coma, lowering of attention, speech disorders, Parkinson's disease and autism.

The compounds of formulae P and Q are also effective for treating sexual dysfunction in both males and females. Disorders of this type include, for example, erectile dysfunction and orgasmic dysfunction related to clitoral disturbances.

Compounds of the present invention are also useful in the treatment of substance abuse, including for example addiction to cocaine, heroin, nicotine, alcohol, anxiolytic and hypnotic drugs, cannabis (marijuana), amphetamines, hallucinogens, phenylcyclidine, volatile solvents, and volatile nitrites. Nicotine addiction includes nicotine addiction of all known forms, such as, for example, nicotine addiction resulting from cigarette, cigar and/or pipe smoking, as well as addiction resulting from tobacco chewing. In this respect, due to their activity as norepinephrine and dopamine uptake inhibitors, the compounds of the present invention function in a manner similar to that of buproprion (ZYBAN®, GlaxoSmithKline, Research Triangle Park, N.C., USA), by reducing the craving for the nicotine stimulus. As a benefit beyond the therapeutic activity of buproprion, however, the compounds of the present invention provide an additional serotonergic component.

Compounds of the present invention are also effective in the prophylaxis of migraine.

The magnitude of a prophylactic or therapeutic dose of a compound of formula A-F, P or Q will vary with the nature and severity of the condition to be treated and the route of administration. The dose, and perhaps the dose frequency, will also vary according to the age, body weight and response of the individual patient. In general, the total daily dose ranges of compounds of the present invention will be from about 25 mg per day to about 1000 mg per day, preferably about 100 mg per day to about 600 mg per day, in single or divided doses.

It is further recommended that children, patients over 65 years old, and those with impaired renal or hepatic function, initially receive low doses and that the dosage be titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Any suitable route of administration may be employed. For example, oral, rectal, intranasal, and parenteral (including subcutaneous, intramuscular, and intravenous) routes may be employed. Dosage forms can include tablets, troches, dispersions, suspensions, solutions, capsules and patches.

Pharmaceutical compositions of the present invention include as active ingredient, a single compound, or a mixture of compounds, of formula A-F, P or Q, or a pharmaceutically acceptable salt of P or Q, together with a pharmaceutically acceptable carrier and, optionally, with other therapeutic ingredients.

The term "pharmaceutically acceptable salt thereof" refers to salts prepared from pharmaceutically acceptable non-toxic acids including inorganic acids and organic acids. Exemplary acids that form pharmaceutically acceptable salts with the amines of the invention, and that may be used in the compositions of the present invention are acetic acid, benzenesulfonic (besylate) acid, benzoic acid, isethionic acid, camphorsulfonic acid, citric acid, ethenesulfonic acid, fumaric acid, gluconic acid, glutamic acid, hydrobromic acid, hydrochloric acid, lactic acid, maleic acid, malic acid, mandelic acid, methanesulfonic acid, mucic acid, nitric acid, pamoic acid, pantothenic acid, phosphoric acid, succinic acid, sulfuric acid, p-toluenesulfonic acid and tartaric acid. The hydrochloric acid salt is particularly preferred.

Compositions suitable for oral, rectal, and parenteral administration are encompassed by the present invention. A preferred route of administration is oral. The compositions may be conveniently presented in unit dosage form and prepared by any of the methods well known in the art of pharmacy. Preferred unit dosage formulations are those containing a therapeutically effective dose, or an appropriate fraction thereof, of the active ingredient(s).

The compositions of the present invention will also include a pharmaceutically acceptable carrier. The carrier may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by a standard aqueous or nonaqueous techniques. Oral and parenteral sustained release dosage forms may also be used.

Oral syrups, as well as other oral liquid formulations, are well known to those skilled in the art, and general methods for preparing them are found in any standard pharmacy school textbook, for example *Remington: The Science and Practice of Pharmacy*. Chapter 86 of the 19th edition of Remington entitled "Solutions, Emulsions, Suspensions and Extracts" describes in complete detail the preparation of syrups (pages 1503-1505) and other oral liquids.

Similarly, sustained release formulation is well known in the art, and Chapter 94 of the same reference, entitled "Sustained-Release Drug Delivery Systems," describes the more common types of oral and parenteral sustained-release dosage forms (pages 1660-1675.) The relevant disclosure of each of these chapters is incorporated herein by reference. Because they reduce peak plasma concentrations, as compared to conventional oral dosage forms, controlled release dosage forms are particularly useful for providing therapeutic plasma concentrations while avoiding the side effects associated with high peak plasma concentrations that occur with conventional dosage forms.

Synthesis of 2-methyl-propane-2-sulfinic acid [4-(3,4-dichlorophenyl)-1,2,3,4-tetrahydro-naphthalen-y-yl]-amide (tetralone t-butanesulfinimine): To a solution of 4-((3,4-dicholorophenyl)-3,4-dihydro-1-naphthalenone (12 g) in THF (40 mL) was added (R)-t-butanesulfinamide (5.2 g) and Ti(OEt)$_4$ (85 mL 20%) in EtOH. The reaction mixture was heated to 60° C. for 13 h. The reaction mixture was cooled to rt, and poured into a brine solution (100 mL) with stirring. The suspension was then added to EtOAc (300 mL) and stirred for 10 min. The suspension was filtered and the filtrate was concentrated to ca 50 mL. One hundred milliliters of EtOAc was added and the organic phase was separated and concentrated to give a crude reaction mixture. The final products were isolated from the crude products by careful flash column chromatography using EtOAc and hexane (3:7 to 1:1) to give ca 3 g starting ketone, and (1R,4S)-4-(3,4-dichlorophenyl)-3,4-dihydro-1-naphthalenone tert-butanesulfinimine (2.5 g, first product) as an oil that solidified on standing.

¹H NMR (CDCl₃) δ 1.33 (S, 9H), 2.10-2.20 (m, 1H), 2.28-2.38 (m, 1H) 2.88-2.98 (m, 1H), 3.34-3.44 (m 1H), 4.12-4.24 (m, 1H), 6.84-6.88 (m, 2H), 7.20 (s, 1H), 7.25-7.40 (m, 3H), 8.22-8.28 (m, 1H). The other product (1R,4R)-4-(3,4-dichloro phenyl)-3-4-dihydro-1-naphthalenone tert-butanesulfinimine (3.0 g, second product, lower R_f) was isolated also as an oil that solidified on standing. ¹H NMR (CDCl₃) δ 1.34 (S, 9H), 2.05-2.18 (m, 1H), 2.28-2.38 (m, 1H), 3.15-3.25 (m, 2H), 4.16-4.22 (m, 1H), 6.84-6.88 (m, 2H), 7.20 (s, 1H), 7.25-7.40 (m, 3H), 8.22-8.28 (m, 1H).

Synthesis of (R)-4-(3,4-dichlorophenyl)-3,4-dihydro-1-naphthalenone: (1R,4R)-4-(3,4-dichlorophenyl)3,4-dihydro-1-naphthalenone t-butanesulfinimine (3.0 g, second product) was dissolved in MeOH (20 mL) and concentrated HCl (4 mL) at rt. The reaction mixture was stirred at rt to give a suspension. It was filtered and the solids were washed with hexane to give 1.2 g product. The enantiomeric purity was determined to be >99.3% by HPLC analysis with a ChiralPak AS 10 µm, 4.6×250 mm, Hexane/IPA (90:10), UV 220 nm, R-isomer 8.23 min. S-isomer 12.25 min. ¹H NMR (CDCl₃) δ 2.20-2.32 (m, 1H), 2.42-2.53 (m, 1H) 2.57-2.78 (m, 2H), 4.28 (dd=4.6, 8.1 Hz, 1H), 6.95 (dd, J=2.1, 7.6 Hz, 2H), 7.23 (d J=2.0 Hz, 1H), 7.37-50 (m, 3H), 8.13 (d, J=7.6 Hz, 1H). [α]=−66° (c=1, acetone).

Synthesis of (S)-4-(3,4-dichlorophenyl)-3,4-dihydro-1-naphthalenone. The previous procedure was used, starting from (1R,4S)-4-(3,4-dichlorophenyl)-3,4-dihydro-1-naphthalenone tert-butanesulfinimine. 1.7 g of product (>99% ee) was obtained. [α]=+62 (c=1, acetone). ¹H NMR spectrum of the product is the same as that of its enantiomer.

Synthesis of (1S,4R) and (1R,4R)—N-[4-(3,4-dichlorophenyl)-1,2,3,4-tetrahydro-naphthalen-1-yl]-formamide: (R)-4-(3,4-dichlorophenyl)-3,4-dihydro-1-naphthalenone (1.2 g) was added formic acid (3 mL) and formamide (3 mL). The reaction mixture was heated to 160-165° C. for 15 h under nitrogen atmosphere. The reaction mixture was cooled to rt and decanted the solvent. The residue solids was passed through flash column using EtOAc:Hexane (3:7 to 1:1) to give the (1R,4R)-formamide (400 mg, first spot), and the (1S,4R)-formamide (360 mg). ¹H NMR of the first product [(1R,4R)-isomer]: (CDCl₃) δ 1.80-2.10 (m, 3H), 2.10-2.20 (m, 1H), 4.00-4.10 (m, 1H), 5.22-5.30 (m, 1H), 6.10-6.20 (m, 1H), 6.80-6.90 (M, 1H), 6.90-6.96 (m, 1H), 7.10-7.40 (m, 5H), 8.22 (s, 1H). M+320. ¹H NMR of the second product [(1S,4R)-isomer: δ 1.64-1.90 (m, 2H), 2.10-2.28 (m, 2H), 4.10 (m, 1H), 5.38-5.42 (m, 1H), 5.82-6.05 (m, 1H), 6.80-6.90 (m, 2H), 7.10-40 (m, 5H), 8.28 (s, 1H). Mass Spec. M⁺ 320.

Synthesis of (1S,4R)-trans 4-(3,4-dichlorophenyl)-1,2,3,4-tetrahydro-1-napthalenamine HCl: (1S,4R) formamide (ca 300 mg) was dissolved in MeOH (5 mL) followed by addition of 6N HCl (6 mL). The reaction mixture was heated to 80° C. for 2 h. The reaction mixture was cooled to rt for 1 h and filtered to collect the solid. It was washed with acetone (3 mL) and dried to give the product (280 mg). Enantiomeric purity was determined to be >99.8% by HPLC analysis with a ChiralPak AD 10 µm, 4.6×250 mm, Hexane/IPA/DEA (99:1:0.1), UV 220 nm, (1R,4S)-isomer 11.00 min. (1S,4R)-isomer 11.70 min [α]=−51° (C=1, MeOH). ¹H NMR (CD₃OD) δ 1.86-1.97 (m, 2H), 2.20-2.42 (m, 2H), 4.30 (broad s, 1H), 4.67 (broad s, 1H), 4.87 (s, 3H), 6.95-6.99 (m, 2H), 7.18 (s, 1H), 7.28-7.50 (m, m, 4H). M⁺ 293.

Synthesis of (1R,4S)-trans 4-(3,4-dichlorophenyl)-1,2,3,4-tetrahydro-1-napthalenamine HCl: It was obtained similarly from (1R,4S) formamide with HCl hydrolysis. Ee of the product is >99.8% based on HPLC analysis with a ChiralPak AD 10 µm, 4.6×250 mm, Hexane/IPA/DEA (99:1:0.1), UV 220 nm, (1R,4S)-isomer 11.00 min. (1S,4R)-isomer 11.70 min.

Synthesis of (1R,4R)-cis 4-(3,4-dichlorophenyl)-1,2,3,4-tetrahydro-1-napthalenamine HCl: It was obtained similarly from (1R,4R) formamide with HCl hydrolysis. Enantiomeric purity was determined to be 96.8% by HPLC analysis with a ChiralPak AD 10 µm, 4.6×250 mm, Hexane/IPA/DES (99:1:0.1), UV 220 nm, (1R,4R)-isomer 11.84 min. (1S,4S)-isomer 9.80 min. ¹H NMR (CD₃OD) δ 1.96-2.26 (m, 4H), 4.14-4.22 (m, 1H), 4.54-4.63 (m, 1H), 4.87 (s, 3H), 7.88-7.94 (m, 1H), 7.18-7.20 (m, 1H), 7.30-7.50 (m, 5H). Mass Spec M⁺ 292.

Synthesis of (1S,4S)-cis 4-(3,4-dichlorophenyl)-1,2,3,4-tetrahydro-1-napthalenamine HCl: It was obtained similarly from (1S,4S) formamide. Ee of the product was 98.5% by HPLC analysis. ¹H NMR spectrum is the same as the enantiomer. Mass Spec M⁺ 292.

The compounds of the invention were tested for their inhibition of functional uptake of serotonin (5-HT), norepinephrine (NE), or dopamine (DA), in synaptosomes prepared from rat whole brain, hypothalamus, or corpus striatum, respectively. Compounds were tested initially at 10 µM in duplicate, and if ≥50% inhibition of uptake was observed, they were tested further at 10 different concentrations in duplicate in order to obtain full inhibition curves. IC$_{50}$ values (concentration inhibiting control activity by 50%) were then determined by nonlinear regression analysis of the inhibition curves and tabulated below.

Experimental Conditions for Monoamine Uptake Assays
Serotonin Functional Uptake Assay Characterization of serotonin uptake is performed using synaptosomes isolated in a 0.32M sucrose buffer from a male Wistar rat cortex. The uptake of radiolabelled serotonin by synaptosomes (100 µg of proteins/point) is allowed by incubating them in a deep well for 15 min at 37° C. in presence of test compounds and [³H]5-hydroxytryptamine (0.1 µCi/point).

Synaptosomes and [³H]5-hydroxytryptamine are prepared in a Krebs buffer pH 7.4 containing 25 mM NaHCO₃, 11 mM glucose and 50 µM ascorbic acid. This incubation buffer is oxygenated during 5 minutes before incubation. Basal control is incubated for 15 minutes at 4° C. in order to avoid any uptake. Following this incubation the uptake is stopped by filtration through an "unifilter 96-wells GFB Packard plate" washed with Krebs buffer containing 25 mM NaHCO₃ in order to eliminate the free [³H]5-hydroxytryptamine. The radioactivity associated to the synaptosomes retained onto the unifilter corresponding to the uptake is then measured with a microplate scintillation counter Topcount, Packard using a scintillation liquid microscint 0, Packard.

The reference compound is imipramine tested at 10 concentrations ranging from 10⁻¹¹ M to 10⁻⁵ M in order to obtain an IC$_{50}$ value. See, Perovics and Müller, "Pharmacological profile of hypericum extract: effect on serotonin uptake by postsynaptic receptors," *Arzeim. Forsch./Drug Res.*, 45:1145-1148 (1995).

Dopamine Functional Uptake Assay

Characterization of dopamine uptake is performed using synaptosomes isolated at Cerep in a 0.32 M sucrose buffer from a male Wistar rat striatum. The uptake of radiolabelled dopamine by synaptosomes (20 µg of proteins/point) is allowed by incubating them for 15 minutes at 37° C. in presence of test compounds and [³H]-dopamine (0.1 µCi/point). The experiment is performed in a deep well. Synaptosomes and [³H]-dopamine are prepared in a Krebs buffer pH 7.4 containing 25 mM NaHCO₃, 11 mM glucose and 50 µM ascorbic acid. This incubation buffer is oxygenated during 5 minutes before incubation. Basal control is incubated for 15 minutes at 4° C. in order to avoid any uptake. Following this incubation the uptake is stopped by filtration through an "unifilter 96-wells GFB Packard plate" washed with Krebs buffer containing 25 mM NaHCO$_3$ in order to eliminate free [$^3$H]-dopamine. The radioactivity associated to the synaptosomes retained onto the unifilter corresponding to the uptake is then measured with a microplate scintillation counter Topcount, Packard using a scintillation liquid microscint 0, Packard. The reference compound is GRB12909 tested at 8 concentrations ranging from 10$^{-11}$ M to 10$^{-6}$ M in order to obtain an IC$_{50}$ value. See, Jankowsky et al., "Characterization of sodium-dependent [$^3$H]GBR-12935 binding in brain: a radioligand for selective labeling of the dopamine transport complex," *J. Neurochem*, 46:1272-1276 (1986).

Norepinephrine Functional Uptake Assay

Characterization of norepinephrine uptake is performed using synaptosomes isolated at Cerep in a 0.32 M sucrose buffer from a male Wistar rat hypothalamus. The uptake of radiolabeled norepinephrine by synaptosomes (100 µg of proteins/point) is allowed by incubating them for 20 minutes at 37° C. in presence of test compounds and [$^3$H]-norepinephrine (0.1 µCi/point). The experiment is performed in a deep well.

Synaptosomes and [$^3$H]-norepinephrine are prepared in a Krebs buffer pH 7.4 containing 25 mM NaHCO$_3$, 11 mM glucose and 50 µM ascorbic acid. This incubation buffer is oxygenated during 5 minutes before incubation. Basal control is incubated for 20 minutes at 4° C. in order to avoid any uptake. Following this incubation the uptake is stopped by filtration through an "unifilter 96-wells GFB" Packard plate washed with Krebs buffer containing 25 mM NaHCO$_3$ in order to eliminate the free [$^3$H]-norepinephrine. The radioactivity associated to the synaptosomes retained onto the unifilter corresponding to the uptake is then measured with a microplate scintillation counter Topcount, Packard using a scintillation liquid microscint 0, Packard.

The reference compound is imipramine tested at 13 concentrations ranging from 10$^{-11}$ M to 10$^{-5}$ M in order to obtain an IC$_{50}$ value. See, Perovics and Müller, "Pharmacological profile of hypericum extract: effect on serotonin uptake by postsynaptic receptors," *Arzeim. Forsch./Drug Res.*, 45:1145-1148 (1995). The results of the monoamine uptake assays are provided in Table 1.

TABLE 1

IC$_{50}$ Values (µM) for Compounds of the
Invention in Functional Monoamine Uptake Assays

|  | 5-HT | NE | DA |
| --- | --- | --- | --- |
| sertraline | 0.0016 | 0.31 | 0.048 |
| P | 0.0077 | 0.0096 | 0.0064 |
| Q | 0.088 | 0.035 | 0.019 |
| P + Q | 0.041 | 0.0088 | 0.0071 |
| imipramine (standard) | 0.054/0.051 | — | — |
| protriptyline (standard) | — | 0.0036 | — |
| GBR 12909 (standard) | — | — | 0.0028/0.0051/0.0034 |

/ separates multiple determinations
— <50% inhibition

As shown in Table 1, P and Q exhibit similar inhibitory potency on the neuronal uptake of NE, DA, and 5HT. Currently, the therapeutic approach to treating affective disorders in man is the selective inhibition of a single monoamine uptake mechanism or the dual inhibition of two of these molecular targets. The equipotent inhibition of the neuronal uptake of NE, DA and 5HT provides the clinician with the ability to more effectively treat affective disorders and eating disorders by elevating all of the monoamine levels in the brain simultaneously and over the same dose-range without the need to titrate separate drugs. For those CNS disorders that are presently treated with dopaminergic, norepinephrine or mixed DA-NE uptake inhibitors (e.g. OCD, ADD, ADHD, sexual dysfunction and substance abuse), the equipotent inhibition of the neuronal uptake of NE, DA and 5HT provides more effective treatment by adding the serotonergic effect.

The results of the monoamine uptake assays for compounds A-F are provided in Table 3.

TABLE 3

IC$_{50}$ Values (µM) for Formamides A-F
in Functional Monoamine Uptake Assays

| N-[4-(3,4-dichlorophenyl)-1,2,3,4-tetrahydronaphthalen-1-yl]formamide | 5-HT | NE | DA |
| --- | --- | --- | --- |
| (R,S/S,R) trans = E = A + B | 7.5 | 0.40 | 0.51 |
| (R,R/S,S) cis = F = C + D | — | 3.9 | 0.53 |
| bupropion (positive control) |  | 0.611 | 0.294 |
| sertraline (positive control) | 0.0016 | 0.31 | 0.048 |
| Impiramine (standard) | 0.054/0.051 |  |  |
| Protriptyline (standard) |  | 0.0036 |  |
| GBR 12909 (standard) |  |  | 0.0028/0.0051/0.0034 |

/ separates multiple determinations
empty cell indicates <50% inhibition

As shown in Table 3, the diastereomeric cis and trans N-[4-(3,4-dichlorophenyl)-1,2,3,4-tetrahydronaphthalen-1-yl]formamide exhibit therapeutically useful inhibitory potency on neuronal uptake of dopamine. The trans diastereomer also exhibits a reasonable inhibitory potency on neuronal uptake of norepinephrine.

TABLE 4

Effect of Intraperitoneal Administration of (R,S/S,R) N-[4-(3,4-dichlorophenyl)-1,2,3,4-tetrahydronaphthalen-1-yl]formamide (E)
in the Behavioral Despair Test in Mice (N = 10)

| Compound | Vehicle | Imipramine 10 mg/kg | E 10 mg/kg | E 50 mg/kg |
| --- | --- | --- | --- | --- |
| Immobility | 188 | 64 | 50 | 0 |
| Duration | 183 | 28 | 59 | 15 |
| (sec.) | 167 | 156 | 162 | 0 |
|  | 199 | 98 | 131 | 98 |
|  | 174 | 0 | 22 | 34 |
|  | 158 | 0 | 167 | 59 |
|  | 124 | 63 | 58 | 25 |
|  | 157 | 30 | 135 | 63 |
|  | 179 | 56 | 122 | 0 |
|  | 222 | 116 | 164 | 15 |
| Mean | 175 | 61 | 107 | 31 |
| ±sem | 8 | 16 |  | 10 |
| Dunnett | P < 0.05 | * | * | * |

Vehicle = 1% methylcellulose
* indicates a significant difference vs vehicle for P < 0.05 (Dunnett test)

Exemplary pharmaceutical formulations of the present invention include:

| Tablets - Composition per unit dosage | |
| --- | --- |
| P | 25 mg |
| Croscarmellose | 60 mg |
| colloidal silicon dioxide | 8 mg |
| magnesium stearate | 1 mg |
| microcrystalline cellulose | 190 mg |

-continued

| Tablets - Composition per unit dosage | |
|---|---|
| Croscarmellose | 15 mg |
| Talc | 10 mg |
| Total | 534 mg |

The P (or other compound of the invention) and silicon dioxide are dry mixed, the first portion of croscarmellose is added and the mixture is further dry mixed. The magnesium stearate is added, dry mixed and the mixture is run through a roller compactor and mill. The resulting dry granulate is mixed with the remaining three ingredients and compressed into tablets.

| Powder-filled Capsules - Composition per unit dosage | |
|---|---|
| P | 200 mg |
| Lactose | 250 mg |
| Corn starch | 60 mg |
| magnesium stearate | 5 mg |
| Total | 515 mg |

The P, lactose and cornstarch, in the proportions shown above, are blended until uniform and then the magnesium stearate is blended into the resulting powder, which is sieved and filled into suitably sized, two-piece, hard gelatin capsules using conventional machinery. Other doses may be prepared by altering the fill weight and, if necessary, changing the capsule size to suit.

Pharmaceutical formulations of the formamides A-F may be prepared in similar fashion.

The invention claimed is:

1. A method for treating cerebral function disorder, wherein said cerebral function disorder is lowering of attention, the method comprising administering to a patient in need of treatment for said cerebral function disorder a therapeutically effective amount of a compound of formula PQ:

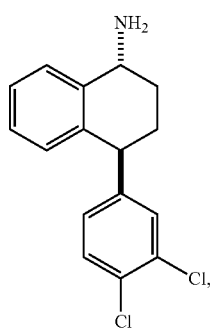

or a salt thereof.

2. A method according to claim 1, wherein the compound of formula PQ is selected from formula P and Q:

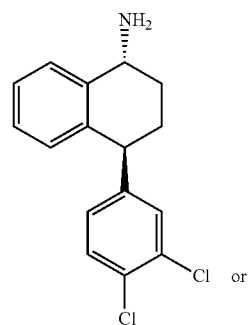

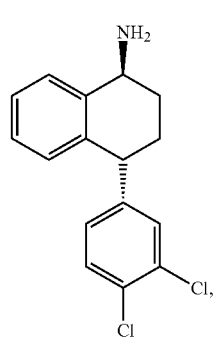

or a salt thereof.

3. A method according to claim 1, wherein the compound of formula PQ is (1S,4R)—N-[4-(3,4-dichlorophenyl)-1,2,3,4-tetrahydro-1-naphthalenamine or a salt thereof.

4. A method according to claim 1, wherein the compound of formula PQ is (1R,4S)—N-[4-(3,4-dichlorophenyl)-1,2,3,4-tetrahydro-1-naphthalenamine or a salt thereof.

5. A method according to claim 1, wherein the compound of formula PQ is (1S,4R)—N-[4-(3,4-dichlorophenyl)-1,2,3,4-tetrahydro-1-naphthalenamine hydrochloride.

6. A method according to claim 1, wherein the compound of formula PQ is (1R,4S)—N-[4-(3,4-dichlorophenyl)-1,2,3,4-tetrahydro-1-naphthalenamine hydrochloride.

* * * * *